United States Patent [19]
Yanase et al.

[11] Patent Number: 5,916,809
[45] Date of Patent: Jun. 29, 1999

[54] MEDIUM FOR CULTURING NORMAL HUMAN EPIDERMAL MELANOCYTES

[75] Inventors: Hiroshi Yanase, Osaka; Hisashi Torishima, Toyonaka; Ryohei Yamamoto, Chita, all of Japan

[73] Assignee: NEC Corporation, Tokyo, Japan

[21] Appl. No.: 08/822,236

[22] Filed: Mar. 20, 1997

[30] Foreign Application Priority Data

Mar. 22, 1996 [JP] Japan .................................. 8-66100

[51] Int. Cl.⁶ ..................................... C12N 5/00
[52] U.S. Cl. ..................... 435/405; 435/406; 435/407; 435/408
[58] Field of Search .................... 435/404, 405, 435/406, 407, 408

[56] References Cited

U.S. PATENT DOCUMENTS 4,673,649  6/1987  Boyce et al. ............................ 435/240

FOREIGN PATENT DOCUMENTS 6-169761  6/1994  Japan .
6-327470  11/1994  Japan .

OTHER PUBLICATIONS

Tennebaum et al., "Magnesium and Phosphate Enrichment of Culture Medium Stmulates the Proliferation of Epidermal Cells from Newborn and Adult Mice", J. Cell. Physiol. 143(3):431–8 (1990).

Medrano et al., "Successful Culture of Adult Human Melanocytes Obtained from Normal and Vitiligo Donors", J. Invest. Dermatol. 95(4):441–445 (1990).

Hara et al., "Role of Integrins in Melanocyte Attachment and Dendricity" J. Cell Sci. 107(10):2739–48 (1994).

GIBCO Catalog, p. 117 (1992).

Pittelkow et al., "Serum–Free Culture Of Normal Human Melanocytes: Growth Kinetics and Growth Factor Requirements", *Journal of Cellular Physiology*, vol. 140:565–576, (1980).

Boyce et al., "Cultivation, Frozen Storage, and Clonal Growth Of Normal Human Epidermal Keratinocytes In Serum–Free Media", *Journal of Tissue Culture Methods*, vol. 9(2):83–93, (1985).

Boyce et al., "Calcium–Regulated Differentiation Of Normal Human Epidermal Keratinocytes In Chemically Defined Clonal Culture and Serum–Free Serial Culture", *The Journal of Investigative Dermatology*, vol. 81(1):33s–40s, (1983).

Asami et al., "Identification of Trypsin Inhibitor in Bovine Pituitary Extracts As A Survival Factor For Adult Rat Hepatocytes In Primary Culture", *J. Biochem.*, vol. 95(2):299–309, (1984).

*Primary Examiner*—Sandra E. Saucier
*Attorney, Agent, or Firm*—Foley & Lardner

[57] ABSTRACT

Provided is a medium for culturing normal human epidermal melanocytes in vitro. The medium comprises a basal medium for culturing animal cells, $Ca^{2+}$ at a final concentration of between about 0.15 mM and about 1.2 mM and $Mg^{2+}$ at a final concentration of 1.2 mM and 6 mM or $Ca^{2+}$ at a final concentration of between about 0.9 mM and about 1.2 mM and $Mg^{2+}$ at a final concentration between about 0.6 mM and 6.0 mM and 0.001 to 0.1% scrum (v/v). The medium can promote both dendrite formation and proliferation of the cells.

11 Claims, 10 Drawing Sheets

MEDIUM FOR CULTURING NORMAL HUMAN EPIDERMAL MELANOCYTES

BACKGROUND OF THE INVENTION

1. Field of the Invention

The present invention relates to a medium suitable for in vitro culturing normal human epidermal melanocyte.

2. Prior Art

In vitro culturing of normal cells derived from human is a key technique for investigation in many fields including medical and pharmaceutical, or development of drug, cosmetics and the like. Culturing of normal human melanocyte in vitro is a useful steps for studying, such as biosynthesis of melanine in human skin or whitening of the skin. In order to culture said cells, known basal media for culturing animal cells such as MCDB153 or M199 containing supplements, for example growth factors, such as epidermal growth factor and fibroblast growth factor, hormones such as insulin and triiodothyronine, carriers such as cholera toxin and transferrin, bovine pituitary extract, bovine hypothalamus extract and fetal bovine serum (FBS).

However, those conventional media cannot provide enough growth without comparatively large amount of serum. In addition, while the morphology of melanocytes in vivo characterized by dendrite formation and ramification, high population of melanocyte cultured in vitro with a conventional media shows quite different such as bipolar morphology. Dendrite formation of in vitro cultured cells can be promoted by adding an agent that increase intracellular levels of cAMP, such as dbcAMP or IBMX. However, these agents cause suppression of cell proliferation (K, Nakazawa et. al., *Pigment Cell Research* (1993) 6, 406–416).

SUMMARY OF THE INVENTION

An object of the present invention is to provided a medium for in vitro culturing normal human epidermal melanocyte which can promote cell proliferation.

In another object of the present invention is to provide a medium for in vitro culturing normal human epidermal melanocyte which can promote both proliferation and dendrite formation of said cells.

In further object of the present invention is to provide a medium for in vitro culturing normal human epidermal melanocyte which can promote intracellular melanin synthesis of said cells.

According to one aspect of the present invention, there is provided a medium comprising of a basal medium for culturing animal cells, $Ca^{2+}$ at a final concentration of between about 0.9 mM and about 1.2 mM and $Mg^{2+}$ at a final concentration of between about 0.6 mM and 6 mM. In addition, the present invention also provides a medium useful for culturing normal human epidermal melanocyte, comprising of a basal medium for culturing animal cells, $Ca^{2+}$ at a final concentration of between about 0.15 mM and about 1.2 mM and $Mg^{2+}$ at a final concentration of between about 1.2 mM and 6 mM. The most preferable medium according to the present invention contains $Ca^{2+}$ at a final concentration of between about 0.9 mM and about 1.2 mM and $Mg^{2+}$ at a final concentration of between about 1.2 mM and 6 mM.

The medium may further comprise one or more growth factor useful for growth of human melanocyte. The medium of the present invention may still further comprise biological materials such as bovine pituitary extract.

The medium of the present invention may further comprise between about 0.001% and about 0.1% (v/v) of heat inactivated fetal bovine serum.

In another aspect of the present invention, there is provided a method for culturing normal human epidermal melanocyte which contains culturing said cells in the medium of the present invention under cell-culturing conditions.

DETAILED DESCRIPTION OF THE PRESENT INVENTION

Figure 1:
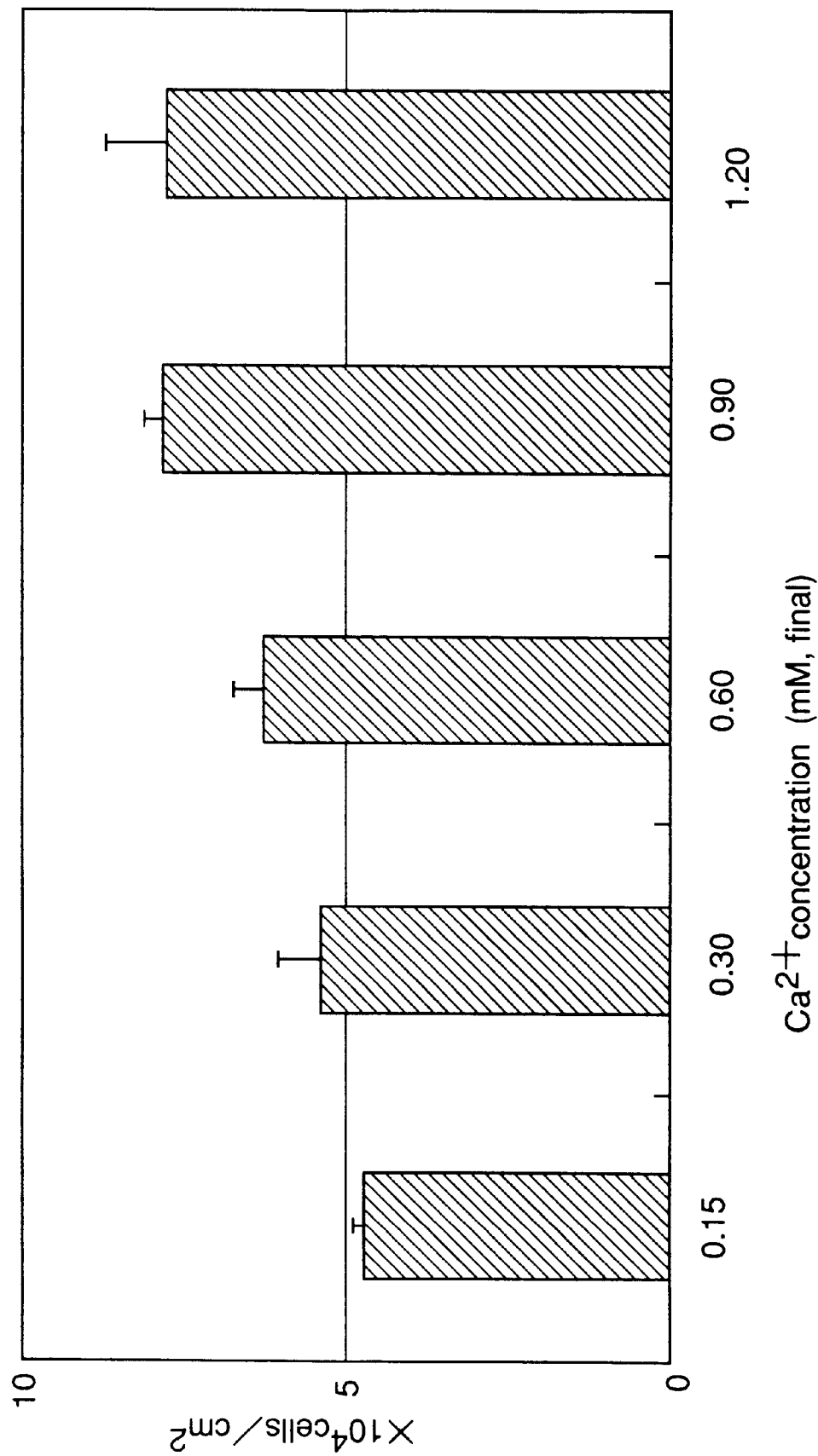
FIG. 1 represents results of example 1.

The inventors found that by controlling $Ca^{2+}$ and $Mg^{2+}$ concentration within a defined range, a basal medium for animal cell culture can be used for in vitro culture of normal human epidermal melanocyte. The medium of the present invention promotes both dendrite formation and proliferation of melanocytes. In addition, melanocyte cultured with the medium of the present invention shows comparatively dark color indicating that the cells can synthesis and deposit comparatively large amount of melanin.

"Basal medium for culturing animal cells" used in the present invention may be any known nutrient medium which is suitable for in vitro culture of normal human epidermal melanocyte. Examples of preferred media include MCDB 153, M199, Eagle's MEM, Dulbecco's modified of Eagle's MEM, HAM F 12, RPMI1640 and the like. Most preferable basal medium is MCDB 153 or modified MCDB 153 which contains enriched amino acid ingredients than standard MCDB 153. In the following table 1 and 2, there are shown the ingredients of standard MCDB 153 and modified MCDB 153. In the present specification, without specific indication, "MCDB 153" represents not only standard MCDB 153 of table 1 but also modified MCDB 153 of table 2. The modified MCDB 153 is identical to the standard MCDB 153 except for containing enriched L-histidine, L-isoleucine, L-methionine HCl, L-phenylalanine, L-tryptophane, and L-tyrosine and supplemented with ethanol amine and phosphoethanol amine.

TABLE 1

Components of standard MCDB 153:

| component | mol/l | mg/l |
|---|---|---|
| L-Alanine | $1.0 \times 10^{-4}$ | 8.91 |
| L-Arginine HCl | $1.0 \times 10^{-3}$ | 210.7 |
| L-Asparagine.H$_2$O | $1.0 \times 10^{-4}$ | 15.01 |
| L-Aspartic Acid | $3.0 \times 10^{-5}$ | 3.99 |
| L-Cysteine HCl.H$_2$O | $2.4 \times 10^{-4}$ | 42.04 |
| L-Glutamic Acid | $1.0 \times 10^{-4}$ | 14.71 |
| L-Glutamine | $6.0 \times 10^{-3}$ | 877.2 |
| Glycine | $1.0 \times 10^{-4}$ | 7.51 |
| L-Histidine HCl.H$_2$O | $8.0 \times 10^{-5}$ | 16.77 |
| L-Isoleucine | $1.5 \times 10^{-5}$ | 1.968 |
| L-Leucine | $5.0 \times 10^{-4}$ | 65.6 |
| L-Lysine HCl | $1.0 \times 10^{-4}$ | 18.27 |
| L-Methionine HCl | $3.0 \times 10^{-5}$ | 4.476 |
| L-Phenylalanine | $3.0 \times 10^{-5}$ | 4.956 |
| L-Proline | $3.0 \times 10^{-4}$ | 34.53 |
| L-Serine | $6.0 \times 10^{-4}$ | 63.06 |
| L-Threonine | $1.0 \times 10^{-4}$ | 11.91 |
| L-Tryptophan | $1.5 \times 10^{-5}$ | 3.06 |
| L-Tyrosine | $1.5 \times 10^{-5}$ | 2.718 |
| L-Valine | $3.0 \times 10^{-4}$ | 35.13 |
| d-Biotin | $6.0 \times 10^{-8}$ | 0.0146 |
| Folic Acid | $1.8 \times 10^{-6}$ | 0.79 |
| DL-alpha-Lipoic Acid | $1.0 \times 10^{-6}$ | 0.2063 |
| Niacinamide | $3.0 \times 10^{-7}$ | 0.03663 |
| D-Pantothenate(Ca) | $1.0 \times 10^{-6}$ | 0.468 |
| Pyridoxine HCl | $3.0 \times 10^{-7}$ | 0.6171 |
| Riboflavin | $1.0 \times 10^{-7}$ | 0.03764 |
| Thiamin HCl | $1.0 \times 10^{-6}$ | 0.3373 |
| Vitamin B$_{12}$ | $3.0 \times 10^{-6}$ | 4.07 |
| Adenine | $1.8 \times 10^{-4}$ | 24.32 |
| Choline Chloride | $1.0 \times 10^{-4}$ | 13.96 |
| D-Glucose | $6.0 \times 10^{-3}$ | 1081 |
| myo-Inositol | $1.0 \times 10^{-4}$ | 18.02 |
| Putrescine 2HCl | $1.0 \times 10^{-6}$ | 0.1611 |
| Sodium Pyruvate | $5.0 \times 10^{-4}$ | 55.0 |
| Thymidine | $3.0 \times 10^{-6}$ | 0.7266 |
| CaCl$_2$.2H$_2$O | $1.5 \times 10^{-4}$ | 22.05 |
| KCl | $1.5 \times 10^{-3}$ | 111.83 |
| MgCl$_2$.6H$_2$O | $6.0 \times 10^{-4}$ | 122.0 |
| NaCl | $1.3 \times 10^{-1}$ | 7599 |
| Na$_2$HPO$_4$.7H$_2$O | $2.0 \times 10^{-3}$ | 536.2 |
| CuSO$_4$.5H$_2$O | $1.1 \times 10^{-8}$ | 0.00275 |
| FeSO$_4$.7H$_2$O | $5.0 \times 10^{-6}$ | 1.39 |
| H$_2$SeO$_3$ | $3.0 \times 10^{-8}$ | 0.003867 |
| MnSO$_4$.5H$_2$O | $1.0 \times 10^{-9}$ | 0.000241 |
| Na$_2$SiO$_3$.9H$_2$O | $5.0 \times 10^{-7}$ | 0.1421 |
| (NH$_4$)$_6$Mo$_7$O$_{24}$.4H$_2$O | $1.0 \times 10^{-9}$ | 0.001236 |
| NH$_4$VO$_3$ | $5.0 \times 10^{-9}$ | 0.000585 |
| NiCl$_2$.6H$_2$O | $5.0 \times 10^{-10}$ | 0.000119 |
| SnCl$_2$.2H$_2$O | $5.0 \times 10^{-10}$ | 0.000113 |
| ZnSO$_4$.7H$_2$O | $5.0 \times 10^{-7}$ | 0.1438 |
| HEPES | $2.8 \times 10^{-2}$ | 6600 |
| NaHCO$_3$ | $1.4 \times 10^{-2}$ | 1176 |
| Sodium Acetate.3H$_2$O | $3.7 \times 10^{-3}$ | 500 |
| Phenol Red(Na) | $3.3 \times 10^{-6}$ | 1.242 |

TABLE 2

Components of modified MCDB 153:

| Component | mol/l | mg/l |
|---|---|---|
| L-Alanine | $1.0 \times 10^{-4}$ | 8.91 |
| L-Arginine HCl | $1.0 \times 10^{-3}$ | 210.7 |
| L-Asparagine.H$_2$O | $1.0 \times 10^{-4}$ | 15.01 |
| L-Aspartic Acid | $3.0 \times 10^{-5}$ | 3.99 |
| L-Cysteine HCl.H$_2$O | $2.4 \times 10^{-4}$ | 42.04 |
| L-Glutamic Acid | $1.0 \times 10^{-4}$ | 14.71 |
| L-Glutamine | $6.0 \times 10^{-3}$ | 877.2 |

TABLE 2-continued

Components of modified MCDB 153:

| Component | mol/l | mg/l |
|---|---|---|
| Glycine | $1.0 \times 10^{-4}$ | 7.51 |
| L-Histidine HCl.H$_2$O | $3.2 \times 10^{-4}$ | 67.08 |
| L-Isoleucine | $7.7 \times 10^{-4}$ | 100.3 |
| L-Leucine | $5.0 \times 10^{-4}$ | 65.6 |
| L-Lysine HCl | $1.0 \times 10^{-4}$ | 18.27 |
| L-Methionine HCl | $1.2 \times 10^{-4}$ | 17.91 |
| L-Phenylalanie | $1.2 \times 10^{-4}$ | 19.82 |
| L-Proline | $3.0 \times 10^{-4}$ | 34.53 |
| L-Serine | $6.0 \times 10^{-4}$ | 63.06 |
| L-Threonine | $1.0 \times 10^{-4}$ | 11.91 |
| L-Tryptophan | $6.0 \times 10^{-5}$ | 12.25 |
| L-Tyrosine | $9.0 \times 10^{-5}$ | 16.31 |
| L-Valine | $3.0 \times 10^{-4}$ | 35.13 |
| d-Biotin | $6.0 \times 10^{-8}$ | 0.0146 |
| Folic Acid | $1.8 \times 10^{-6}$ | 0.79 |
| DL-alpha-Lipoic Acid | $1.0 \times 10^{-6}$ | 0.2063 |
| Niacinamide | $3.0 \times 10^{-7}$ | 0.03663 |
| Ethanolamine | $1.0 \times 10^{-4}$ | 6.108 |
| Phosphoethanolamine | $1.0 \times 10^{-4}$ | 14.106 |
| D-Pantothenate(Ca) | $1.0 \times 10^{-6}$ | 0.468 |
| Pyridoxine HCl | $3.0 \times 10^{-7}$ | 0.06171 |
| Riboflavin | $1.0 \times 10^{-7}$ | 0.03764 |
| Thiamin HCl | $1.0 \times 10^{-6}$ | 0.3373 |
| Vitamin B$_{12}$ | $3.0 \times 10^{-6}$ | 4.07 |
| Adenine | $1.8 \times 10^{-4}$ | 24.32 |
| Choline Chloride | $1.0 \times 10^{-4}$ | 13.96 |
| D-Glucose | $6.0 \times 10^{-3}$ | 1081 |
| myo-Inositol | $1.0 \times 10^{-4}$ | 18.02 |
| Putrescine 2HCl | $1.0 \times 10^{-6}$ | 0.1611 |
| Sodium Pyruvate | $5.0 \times 10^{-4}$ | 55.0 |
| Thymidine | $3.0 \times 10^{-6}$ | 0.7266 |
| CaCl$_2$.2H$_2$O | $1.5 \times 10^{-4}$ | 22.05 |
| KCl | $1.5 \times 10^{-3}$ | 111.83 |
| MgCl$_2$.6H$_2$O | $6.0 \times 10^{-4}$ | 122.0 |
| NaCl | $1.3 \times 10^{-1}$ | 7599 |
| Na$_2$HPO$_4$.7H$_2$O | $2.0 \times 10^{-3}$ | 536.2 |
| CuSO$_4$.5H$_2$O | $1.1 \times 10^{-8}$ | 0.00275 |
| FeSO$_4$.7H$_2$O | $5.0 \times 10^{-6}$ | 1.39 |
| H$_2$SeO$_3$ | $3.0 \times 10^{-8}$ | 0.003867 |
| MnSO$_4$.5H$_2$O | $1.0 \times 10^{-9}$ | 0.000241 |
| Na$_2$SiO$_3$.9H$_2$O | $5.0 \times 10^{-7}$ | 0.1421 |
| (NH$_4$)$_6$Mo$_7$O$_{24}$.4H$_2$O | $1.0 \times 10^{-9}$ | 0.001236 |
| NH$_4$VO$_3$ | $5.0 \times 10^{-9}$ | 0.000585 |
| NiCl$_2$.6H$_2$O | $5.0 \times 10^{-10}$ | 0.000119 |
| SnCl$_2$.2H$_2$O | $5.0 \times 10^{-10}$ | 0.000113 |
| ZnSO$_4$.7H$_2$O | $5.0 \times 10^{-7}$ | 0.1438 |
| HEPES | $2.8 \times 10^{-2}$ | 6600 |
| NaHCO$_3$ | $1.4 \times 10^{-2}$ | 1176 |
| Sodium Acetate 3H$_2$O | $3.7 \times 10^{-3}$ | 500 |
| Phenol Red(Na) | $3.3 \times 10^{-6}$ | 1.242 |

According to the present invention, at least one of $Ca^{2+}$ and $Mg^{2+}$ concentrations is enriched from the basal medium. The final $Ca^{2+}$ concentration of the medium of the present invention is in the range between about 0.15 mM and about 1.2 mM, preferably, about 0.9 mM and about 1.2 mM. However, when $Ca^{2+}$ concentration is lower than 0.9 mM, final concentration of $Mg^{2+}$ is adjusted in the range of between about 1.2 mM and 1.8 mM. The final concentration of $Ca^{2+}$ can be adjusted by adding $Ca^{2+}$ source such as $CaCl_2$ into the basal medium.

The final $Mg^{2+}$ concentration of the medium of the present invention is in the range between about 0.6 mM and about 6 mM, preferably, about 1.2 mM and about 1.8 mM. However, when $Mg^{2+}$ concentration is lower than 1.2 mM, a final concentration of $Ca^{2+}$ is adjusted to more than 0.9 mM. The final concentration of $Mg^{2+}$ can be adjusted by adding $Mg^{2+}$ source such as $MgCl_2$ and $MgSO_4$ into the basal medium.

The medium of the present invention may further comprise various supplements that are employed in conventional animal cell in vitro culture, if desired. For example, one or more growth factors such as epidermal growth factor (EGF), basic fibroblast growth factor (bFGF), Interleukin-1, transforming growth factor alpha and the like, are preferably contained in the medium.

The medium of the present invention preferably contains comparatively small amount of serum. Examples for serum include that of derived from bovine, horse, porcine and the like. Among them, fetal bovine serum is most preferable because of its commercial availability. In the medium of the present invention, serum may be contained at a final concentration of between about 0.001% and about 1%(v/v), more preferably between about 0.001% and about 0.1% (v/v).

Further, the medium of the present invention may comprise biological materials for example bovine pituitary extract (BPE), bovine hypothalamus extract, bovine cerebrum extract and albumin; insulin, phorbol 12 myristrate 13-acetate(PMA), heparin, hydrocortisone, transferrin, cholera toxin, and triiodothyronine. Further more, the medium may comprise antibiotics such as gentamicin sulfate, amphotericin B, penicillin, mitomycin, kanamycin sulfate and streptomycin. These supplements described above may be added into the medium singly or in mixture as required.

The present invention also provides a method for culturing normal human epidermal melanocyte in a medium of the present invention. According to the method of the present invention, the normal human epidermal melanocyte may be the cells freshly derived from any age and any sexes of human, successively cultured cells of such freshly derived cells, or both of freshly derived and successively cultured cells which are preserved by conventional frozen manner.

As the "cell-culture conditions" of the present invention, any conventional conditions for in vitro cell culturing can be employed and it is well known in the art.

To further illustrate the present invention, and not by way of limitation, the following examples are given.

EXAMPLE OF THE INVENTION

Example 1

Normal human epidermal melanocyte culture was performed in modified MCDB 153 with various $Ca^{2+}$ concentrations.

The modified MCDB 153 medium shown in the above table 2 supplemented with the substances shown in following table 3 and fetal bovine serum at a final concentration of 5%(v/v) was used. Final $Ca^{2+}$ concentration of the medium was adjusted with $CaCl_2.2H_2O$ between 0.15 and 1.2 mM. The final $Mg^{2+}$ concentration of 0.6 mM is same as conventional MCDB 153.

TABLE 3

| additives | concentration (final) |
| --- | --- |
| BPE | 0.2% (v/v) |
| Insulin | 10 µg/ml |
| PMA | 20 ng/ml |
| bFGF | 2 ng/ml |
| Heparin | 1 µg/ml |
| hydrocortisone | 0.5 µg/ml |
| transferrin | 1 µg/ml |
| gentamicin sulfate | 50 µg/ml |
| amphotericin B | 50 ng/ml |

Normal human epidermal melanocyte obtained from secondarily cultured cells and stored frozen at liquid nitrogen temperature (Cascade Biologics Inc.) were used. The culture of the cells was performed by using 12-well cell culture plate (Corning). After thawing, the cells were inoculated into the respective media at an initial cell density of 5000 cells/cm². Cells were incubated at 37° C. in 5% $CO_2$ humidified incubator. Cultures were fed fresh media every or every other day. After 7 days incubation, cells were harvested with 0.025% trypsin/0.01% EDTA, and cell numbers were counted. Cell numbers were determined with hemocytometer counting chamber. Results are shown in FIG. 1. Improved cell growth was shown with the medium containing 0.6–0.9 mM of $Ca^{2+}$.

Example 2

The modified MCDB 153 medium shown in the above table 2 supplemented with the substances shown in above table 3 and fetal bovine serum at a final concentration of 5%(v/v) was used. Final $Ca^{2+}$ concentration was adjusted to 0.15 mM (medium 1) and 0.9 mM (medium 2).

Normal human epidermal melanocyte obtained from secondarily cultured cells and stored frozen at liquid nitrogen temperature (Cascade Biologics Inc.) were used. The culture of the cells was performed by using 12-well cell culture plate (Corning). After thawing, the cells were inoculated into the respective media at an initial cell density of 5000 cells/cm². Cells were incubated at 37° C. in 5% $CO_2$ humidified incubator. Cultures were fed fresh media every or every other day.

After 7 days incubation, cells were harvested with 0.025% trypsin/0.01% EDTA, and obtained cell (3rd generation culture) numbers were determined with hemocytometer counting chamber.

Figure 2:
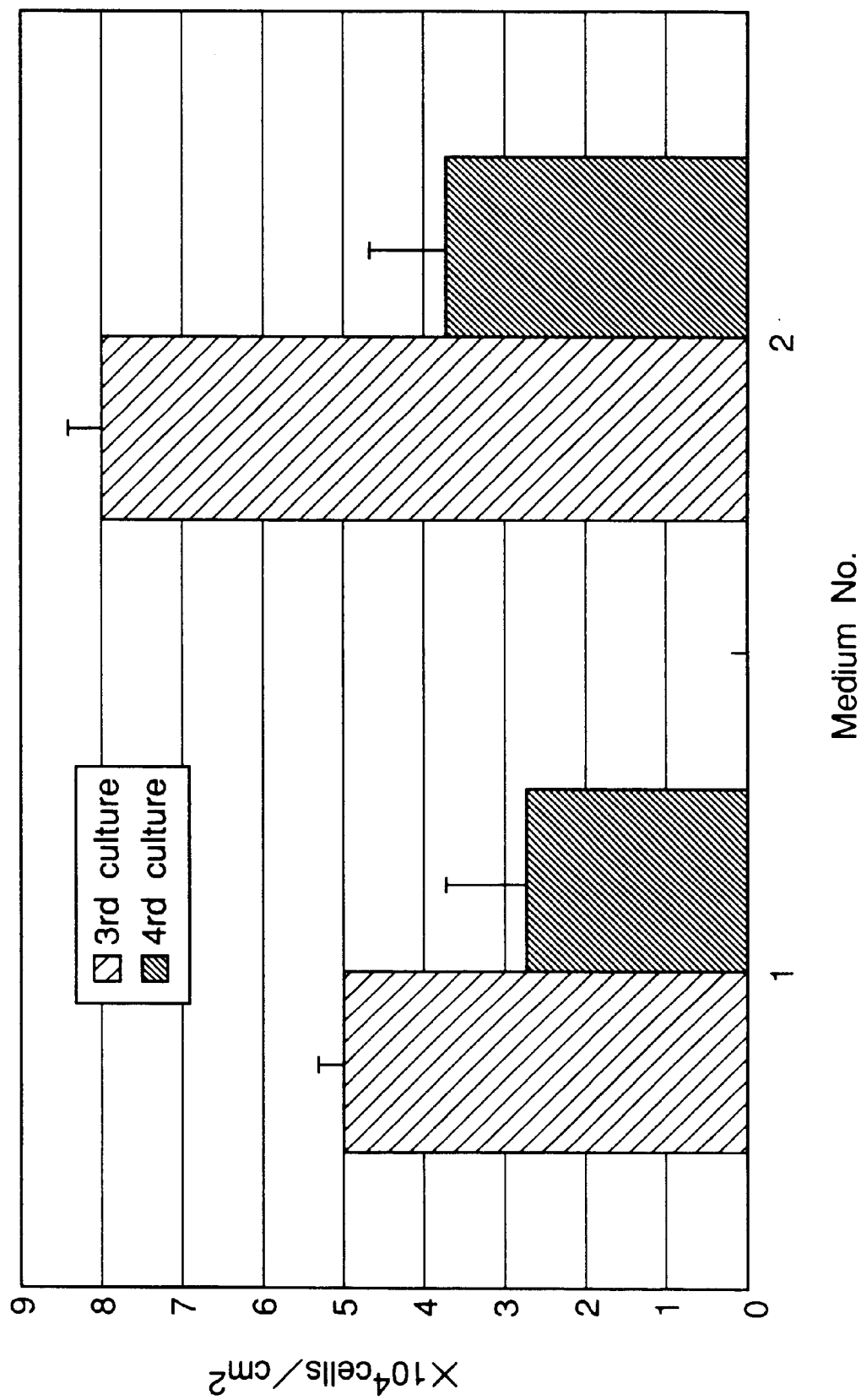
FIG. 2 represents results of example 2.

Then, the obtained cells were washed and inoculated into freshly prepared respective media at an cell density of 5000 cells/cm². The cells were incubated for additional 7 days and then cell numbers of the culture (4th generation culture) were determined as above. Results are shown in FIG. 2.

Improved cell proliferation were observed with the $Ca^{2+}$ enriched medium both of 3rd and 4th generation of cultures.

Example 3

Figure 3:
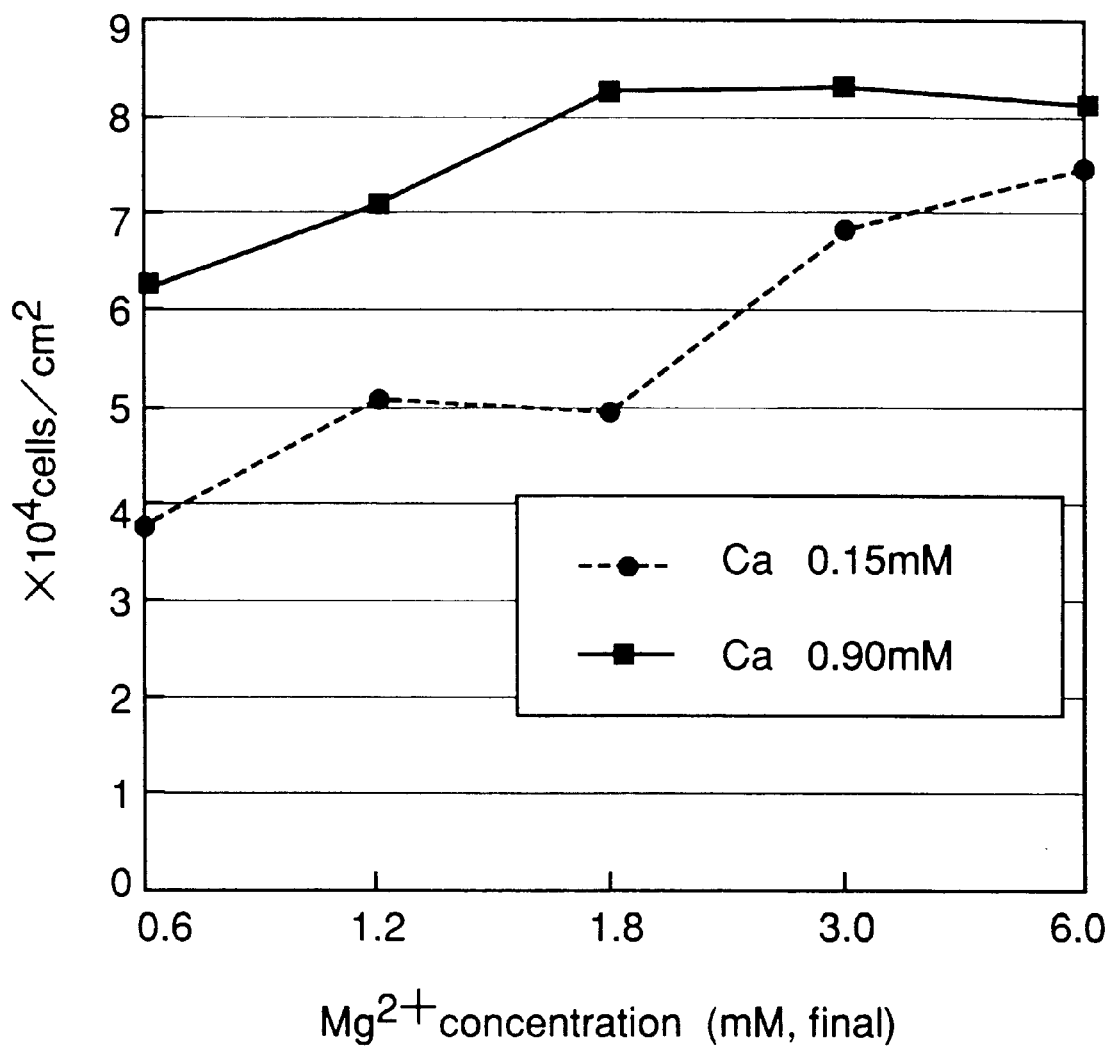
FIG. 3 represents results of example 3.

In to the media of example 2, containing $Ca^{2+}$ at final concentrations of 0.15 mM and 0.9 mM respectively, various amounts of $MgCl_2$ $6H_2O$ were added to provide final $Mg^{2+}$ concentration from 0.6 to 6 mM. Normal human epidermal melanocyte culture was done with said media according to the procedure of example 1. After 7 days incubation, cells were harvested and cell numbers were determined. The results are shown in FIG. 3.

Figure 4:
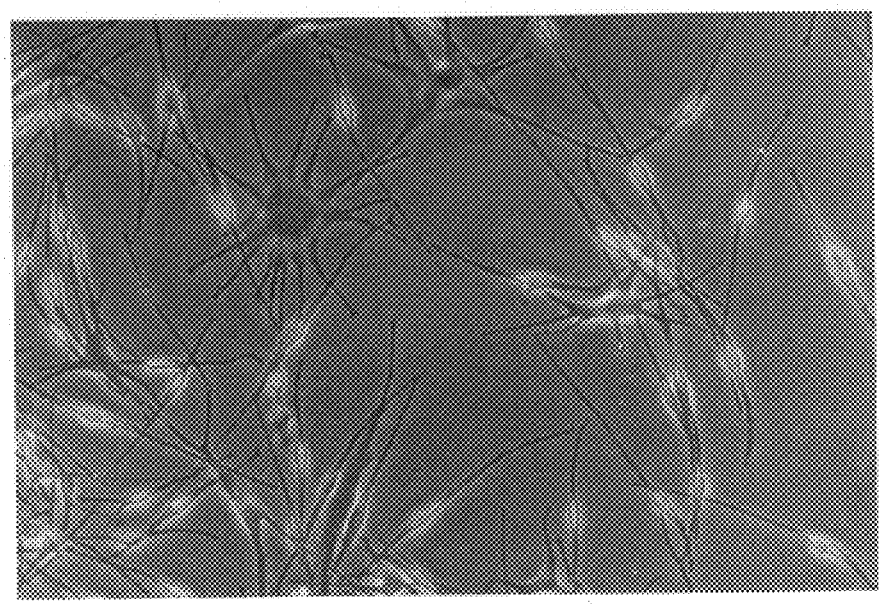
FIG. 4 is a photomicrograph of normal human epidermal melanocyte cultured in a medium containing 0.15 mM of $Ca^{2+}$ and 0.6 mM of $Mg^{2+}$ at 7 days after inoculation. Original magnification×40.
Figure 5:
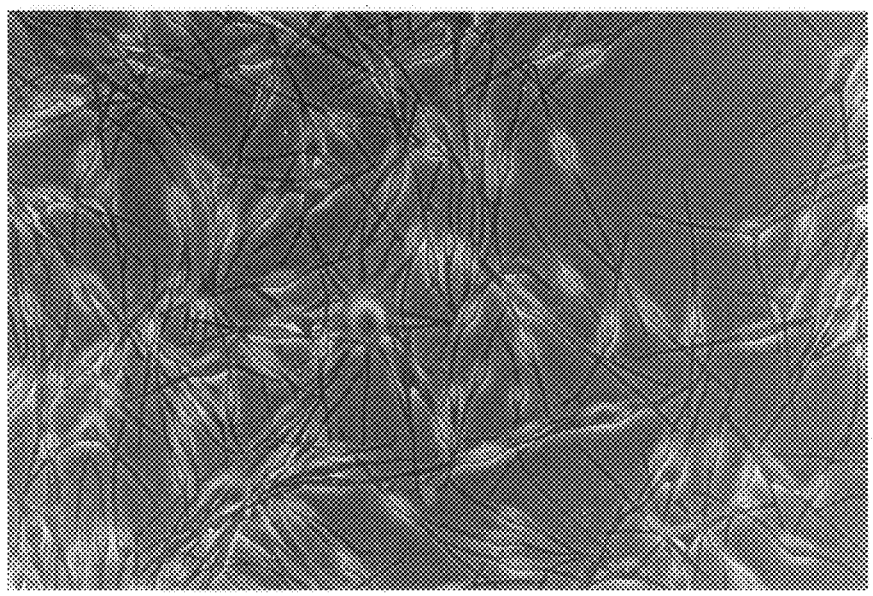
FIG. 5. is a photomicrograph of normal human epidermal melanocyte cultured in a medium containing 0.15 mM of $Ca^{2+}$ and 1.8 mM of $Mg^{2+}$ at 7 days after inoculation in a medium. Original magnification×40.
Figure 6:
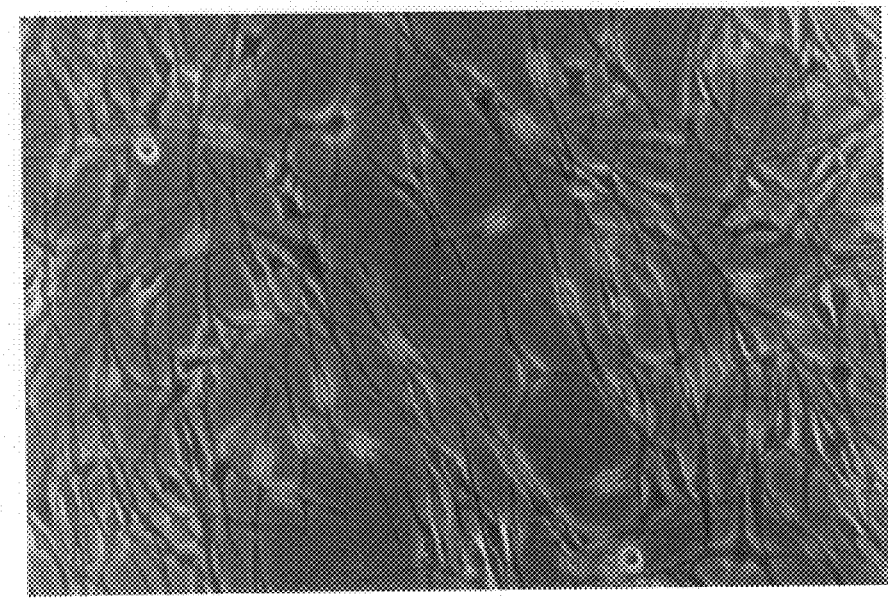
FIG. 6 is a photomicrograph of normal human epidermal melanocyte cultured in a medium containing 0.9 mM of $Ca^{2+}$ and 0.6 mM of $Mg^{2+}$ at 7 days after inoculation. Original magnification×40.
Figure 7:
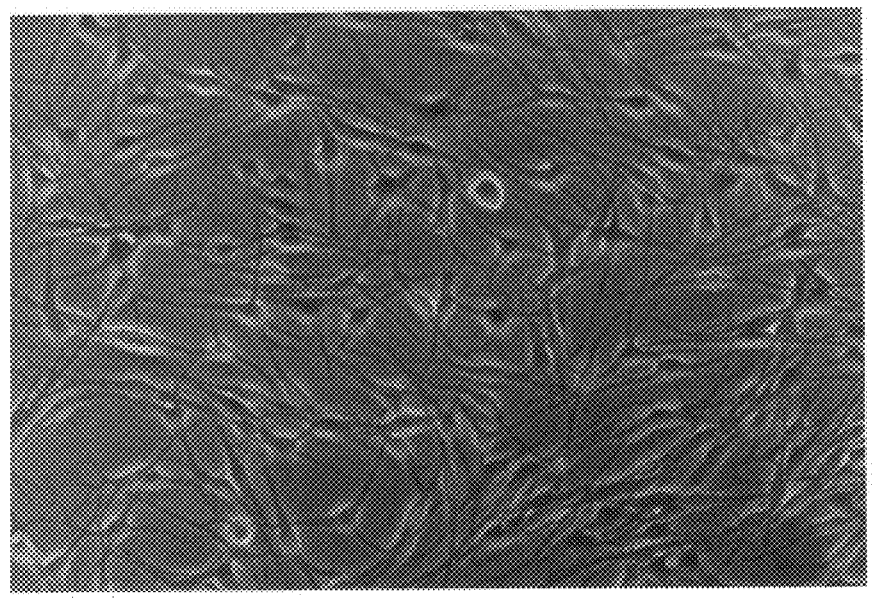
FIG. 7 is a photomicrograph of normal human epidermal melanocyte cultured in a medium containing 0.9 mM of $Ca^{2+}$ and 1.8 mM of $Mg^{2+}$ at 7 days after inoculation. Original magnification×40.
Figure 8:
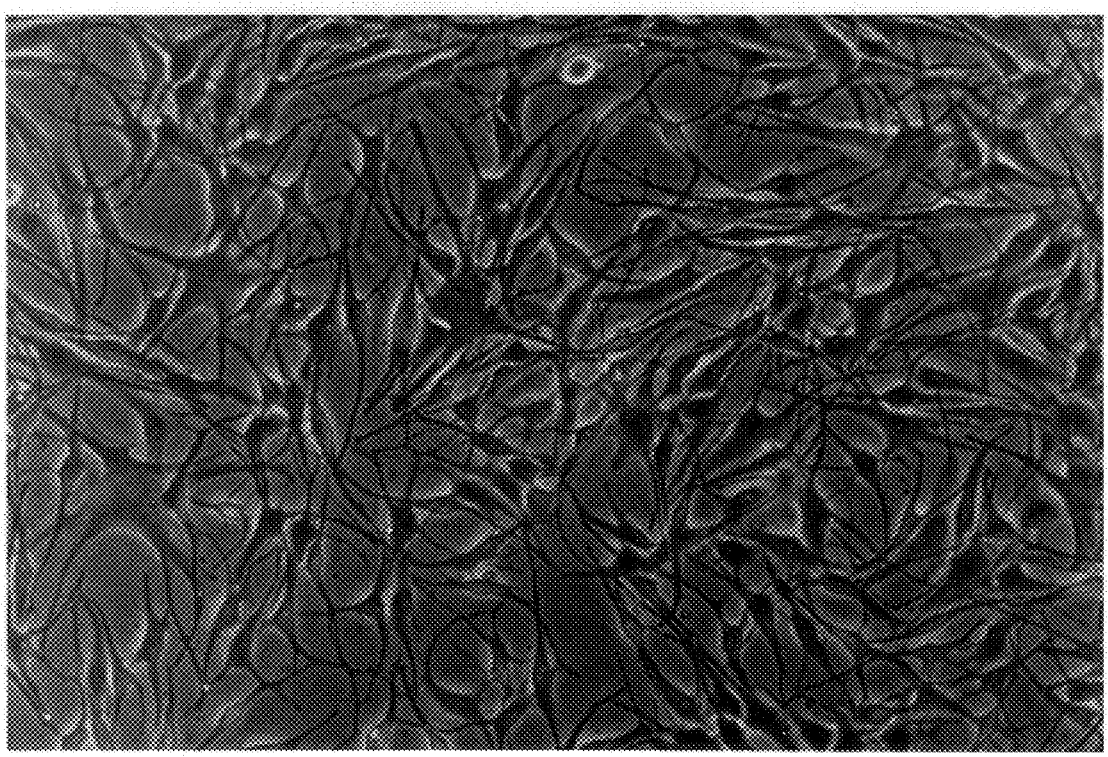
FIG. 8 is a photomicrograph of normal human epidermal melanocyte cultured in a medium containing 0.9 mM of $Ca^{2+}$ and 6.0 mM of $Mg^{2+}$ at 7 days after inoculation. Original magnification×40.

Cell morphology on light microscope in the different culture conditions were shown in FIGS. 4–8. With a modified MCDB 153 containing 0.15 mM of $Ca^{2+}$ and 0.6 mM of $Mg^{2+}$, almost all cells were shown to be bipolar morphology, i.e. having only two ramifications per cell (FIG. 4). With a medium enriched only $Ca^{2+}$ or $Mg^{2+}$, cells were shown to be bipolar morphology, too (FIGS. 5 and 6). In contrast, with media enriched both of $Ca^{2+}$ and $Mg^{2+}$, high population of the cultured cells were shown to be dendrites (FIGS. 7 and 8). In addition, cells cultured with such media were shown comparatively deep color indicating increased intracellular melanin synthesis and deposition (FIGS. 7 and 8).

Example 4

A basal medium shown in following table 4 supplemented with the substances shown in above table 3 and fetal bovine serum at a final concentration of 5%(v/v) were used. Final $Ca^{2+}$ and $Mg^{2+}$ concentrations were adjusted according to table 5 respectively.

Figure 9:
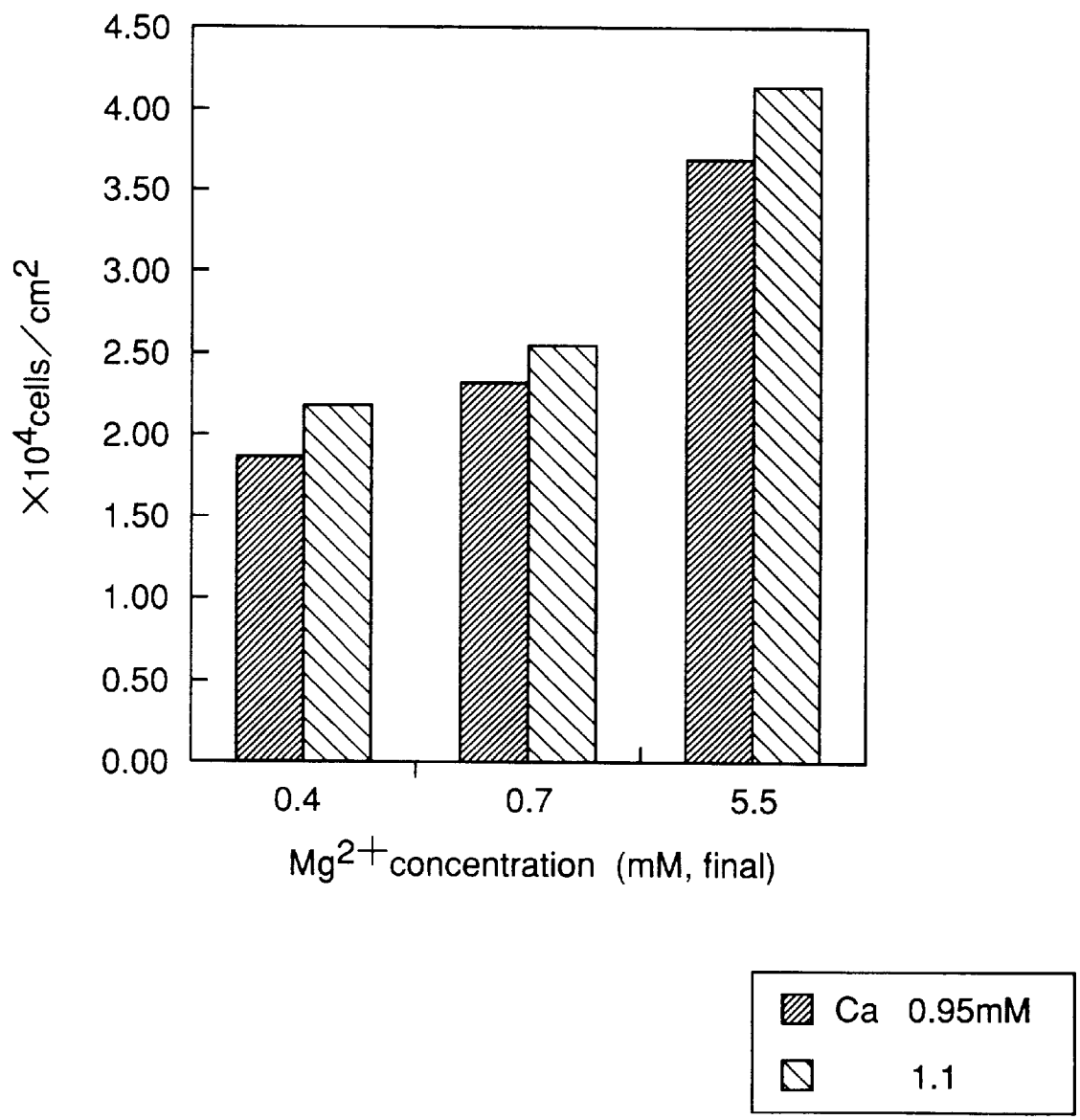
FIG. 9 represents results of example 4.

Normal human epidermal melanocyte were cultured using the above media according to the procedure of example 1. After 5 days incubation, the cells were harvested and cell numbers were determined. The results are shown in FIG. 9.

TABLE 4

Components of basal medium of example 4

| Component | mg/l |
|---|---|
| L-Alanine | 4.45 |
| DL-α-Alanine | 25 |
| L-Arginine HCl | 140.0 |
| L-Asparagine.H$_2$O | 7.51 |
| L-Aspartic Acid | 2.00 |
| DL-Aspartic Acid | 30 |
| L-Cysteine HCl.H$_2$O | 21.26 |
| L-Cystine | 10 |
| L-Glutamic Acid | 7.36 |
| DL-Glutamic Acid.H$_2$O | 75 |
| L-Glutamine | 488.6 |
| Glycine | 28.76 |
| L-Histidine HCl.H$_2$O | 43.5 |
| L-Isoleucine | 50.15 |
| DL-Isoleucine | 20 |
| L-Leucine | 32.8 |
| DL-Leucine | 60 |
| L-Lysine HCl | 44.14 |
| L-Methionine | 8.96 |
| DL-Methionine | 15 |
| L-Phenylalanie | 9.91 |
| DL-Phenylalanine | 25 |
| L-Proline | 32.27 |
| Hydroxy-L-Proline | 5 |
| L-Serine | 31.53 |
| DL-Serine | 25 |
| L-Threonine | 5.96 |
| DL-Threonine | 30 |
| L-Tryptophan | 6.13 |
| DL-Tryptophan | 10.00 |
| L-Tyrosine | 28.16 |
| L-Valine | 17.57 |
| DL-Valine | 25 |
| p-Amino Benzoic acid | 0.025 |
| Ascorbic Acid | 0.025 |
| d-Biotin | 0.012 |
| Folic Acid | 0.4 |
| DL-α-Lipoic Acid | 0.103 |
| Nicotinamide | 0.0308 |
| Nicotinic Acid | 0.0125 |
| Ethanolamine | 3.05 |
| Phosphoethanolamine | 7.05 |
| D-Pantothenate(Ca) | 0.239 |
| Pyridoxal.HCl | 0.0125 |
| Pyridoxine.HCl | 0.0434 |
| α-tocopherol phosphate.2Na | 0.005 |
| Riboflavin | 0.376 |
| Thiamin HCl | 0.174 |
| Vitamin A | 0.05 |
| Vitamin B$_{12}$ | 2.04 |
| Vitamin B$_2$ | 0.05 |
| Vitamin K$_3$ | 0.005 |
| Adenine sulfate | 5 |
| Adenine | 12.2 |
| AMP | 0.1 |
| ATP-2Na | 0.5 |
| Cholesterol | 0.1 |
| Deoxyribose | 0.25 |
| Choline Chloride | 7.23 |
| D-Glucose | 1041 |
| myo-Inositol | 9.035 |
| Glutathione | 0.025 |
| Guanine.HCl | 0.15 |
| Hypoxanthine | 0.15 |
| Xanthine | 0.15 |
| Ribose | 0.25 |

TABLE 4-continued

Components of basal medium of example 4

| Component | mg/l |
|---|---|
| Thymine | 0.15 |
| Tween 80 | 10 |
| Uracil | 0.15 |
| Putrescine.2HCl | 0.0806 |
| Sodium Pyruvate | 27.5 |
| Thymidine | 0.363 |
| CaCl$_2$.2H$_2$O | 11.03 |
| CaCl$_2$ | 70 |
| KCl | 256 |
| MgCl$_2$.6H$_2$O | 61 |
| MgSO$_4$.7H$_2$O | 100 |
| NaCl | 7800 |
| Na$_2$HPO$_4$.7H$_2$O | 268 |
| Na$_2$HPO$_4$.2H$_2$O | 30 |
| KH$_2$PO$_4$ | 30 |
| CuSO$_4$.5H$_2$O | 0.00138 |
| FeSO$_4$.7H$_2$O | 0.695 |
| Fe(NO$_3$)$_3$ | 0.05 |
| H$_2$SeO$_3$ | 0.00193 |
| MnSO$_4$.5H$_2$O | 0.000121 |
| Na$_2$SiO$_3$.9H$_2$O | 0.0711 |
| (NH$_4$)$_6$Mo$_7$O$_{24}$.4H$_2$O | 0.000618 |
| NH$_4$VO$_3$ | 0.000293 |
| NiCl$_2$.6H$_2$O | 0.0000595 |
| SnCl$_2$.2H$_2$O | 0.0000565 |
| ZnSO$_4$.7H$_2$O | 0.0719 |
| HEPES | 3336 |
| NaHCO$_3$ | 1213 |
| Sodium Acetate 3H$_2$O | 250 |
| Sodium Acetate | 25 |
| Phenol Red(Na) | 10 |

TABLE 5

Final concentrations of $Ca^{2+}$ and $Mg^{2+}$

| medium No. | 1 | 2 | 3 | 4 | 5 | 6 |
|---|---|---|---|---|---|---|
| $Ca^{2+}$ (mM) | 0.95 | 0.95 | 0.95 | 1.1 | 1.1 | 1.1 |
| $Mg_{2+}$ (mM) | 0.4 | 0.7 | 5.5 | 0.4 | 0.7 | 5.5 |

Example 5

A basal medium shown in following table 6 supplemented with the substances shown in above table 3 and fetal bovine serum at a final concentration of 5%(v/v) was used. Final $Ca^{2+}$ and $Mg^{2+}$ concentrations were adjusted according to table 7 respectively.

Figure 10:
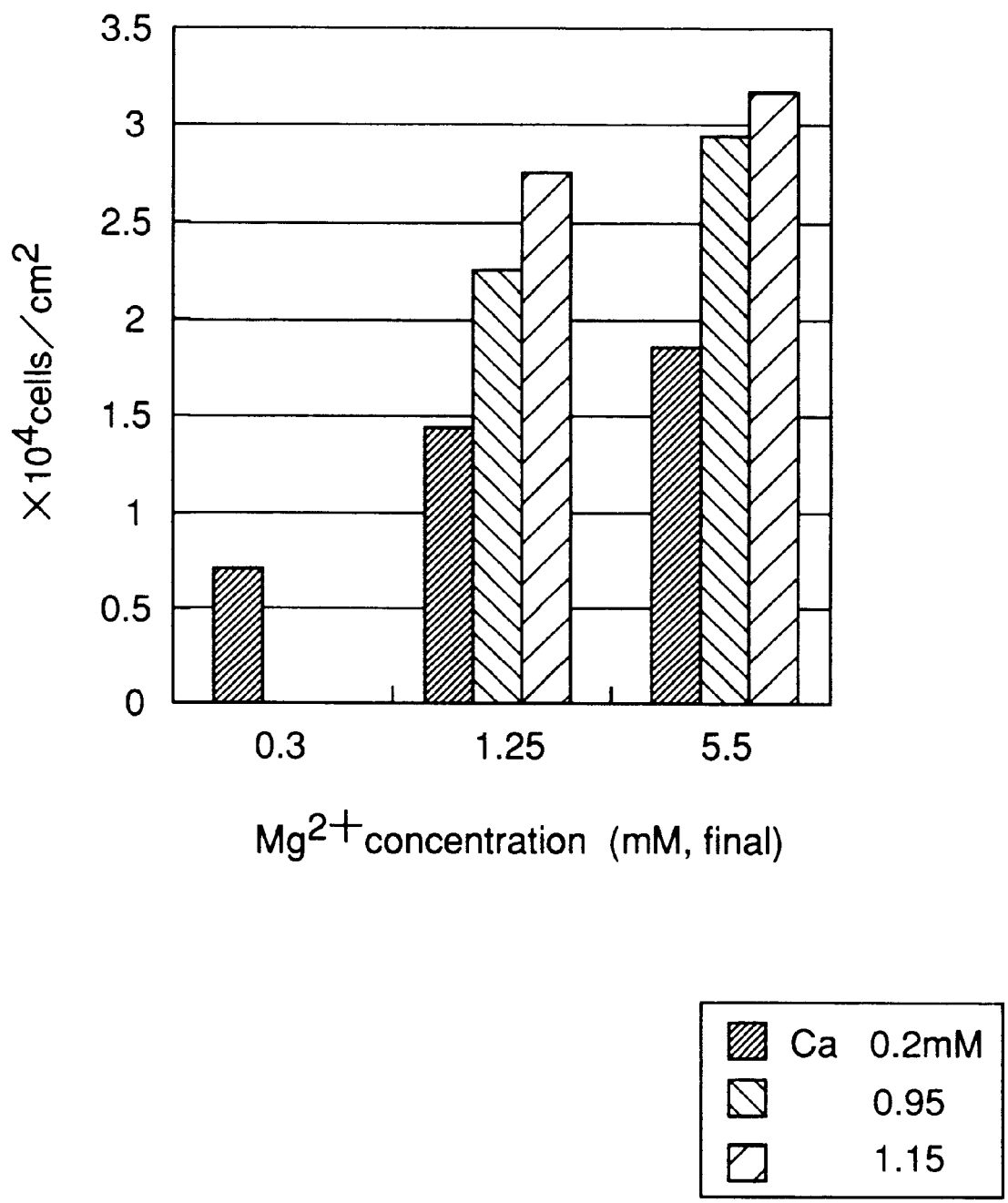
FIG. 10 represents results of example 5.

Normal human epidermal melanocyte were cultured using the above media according to the procedure of example 1. After 5 days incubation, the cells were harvested and cell numbers were determined. The results are shown in FIG. 10.

TABLE 6

Components of basal medium of example 5

| Component | mg/l |
|---|---|
| L-Alanine | 8.96 |
| L-Arginine.HCl | 210.9 |
| L-Asparagine.H$_2$O | 15.01 |
| L-Aspartic Acid | 8.50 |
| L-Cysteine HCl.H$_2$O | 20.01 |
| L-Cystine | 12.5 |
| L-Glutamic Acid | 14.71 |
| L-Glutamine | 511.6 |

TABLE 6-continued

Components of basal medium of example 5

| Component | mg/l |
|---|---|
| Glycine | 7.51 |
| L-Histidine HCl.H$_2$O | 45.0 |
| L-Isoleucine | 51.45 |
| L-Leucine | 39.3 |
| L-Lysine.HCl | 23.64 |
| L-Methionine | 11.20 |
| L-Phenylalanie | 12.41 |
| L-Proline | 23.02 |
| L-Serine | 36.78 |
| L-Threonine | 7.74 |
| L-Tryptophan | 6.43 |
| L-Tyrosine | 9.06 |
| L-Valine | 19.32 |
| d-Biotin | 0.019 |
| Folic Acid | 1.06 |
| DL-alpha-Lipoic Acid | 0.203 |
| Nicotinamide | 0.326 |
| Ethanolamine | 3.05 |
| Phosphoethanolamine | 7.05 |
| D-Pantothenate(Ca) | 0.592 |
| Pyridoxine.HCl | 0.134 |
| Riboflavin | 0.376 |
| Thiamin HCl | 0.669 |
| Vitamin B$_{12}$ | 2.72 |
| Adenine | 12.2 |
| Choline Chloride | 7.33 |
| D-Glucose | 1091 |
| myo-lnositol | 9.281 |
| Hypoxanthine | 2 |
| Putrescine.2HCl | 0.0806 |
| Sodium Pyruvate | 82.5 |
| Thymidine | 0.713 |
| CaCl$_2$.2H$_2$O | 33.08 |
| KCl | 198 |
| MgCl$_2$.6H$_2$O | 61 |
| MgSO$_4$.7H$_2$O | 76.4 |
| NaCl | 7500 |
| Na$_2$HPO$_4$.7H$_2$O | 268 |
| Na$_2$HPO$_4$ | 76.9 |
| KH$_2$PO$_4$ | 41.5 |
| CuSO$_4$.5H$_2$O | 0.00263 |
| FeSO$_4$.7H$_2$O | 1.112 |
| H$_2$SeO$_3$ | 0.00193 |
| MnSO$_4$.5H$_2$O | 0.000121 |
| Na$_2$SiO$_3$.9H$_2$O | 0.0711 |
| (NH$_4$)$_6$Mo$_7$O$_{24}$.4H$_2$O | 0.000618 |
| NH$_4$VO$_3$ | 0.000293 |
| NiCl$_2$.6H$_2$O | 0.0000595 |
| SnCl$_2$.2H$_2$O | 0.0000565 |
| ZnSO$_4$.7H$_2$O | 0.0863 |
| HEPES | 3336 |
| NaHCO$_3$ | 1188 |
| Sodium Acetate 3H$_2$O | 250 |
| Phenol Red(Na) | 0.621 |

TABLE 7

Final concentrations of Ca$^{2+}$ and Mg$^{2+}$

| medium No. | 1 | 2 | 3 | 4 | 5 | 6 | 7 |
|---|---|---|---|---|---|---|---|
| Ca$^{2+}$ (mM) | 0.20 | 0.20 | 0.20 | 0.95 | 0.95 | 1.15 | 1.15 |
| Mg$_{2+}$ (mM) | 0.3 | 1.25 | 5.5 | 1.25 | 5.5 | 1.25 | 5.5 |

Example 6

A basal medium shown in following table 8 supplemented with the substances shown in above table 3 and fetal bovine serum at a final concentration of 5%(v/v) were used. Final Ca$^{2+}$ and Mg$^{2+}$ concentrations were adjusted according to table 9 respectively.

Figure 11:
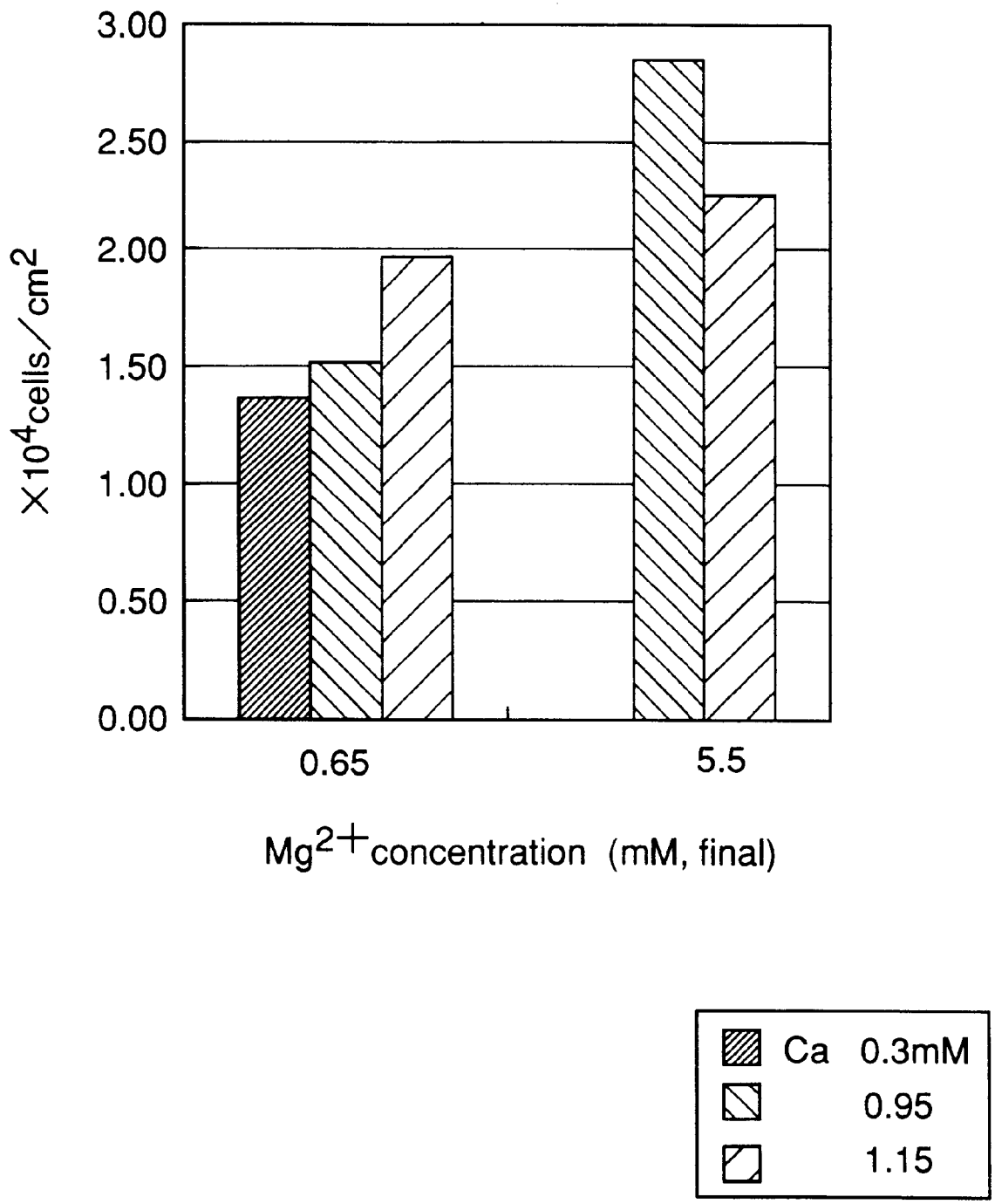
FIG. 11 represents results of example 6.
Figure 12:
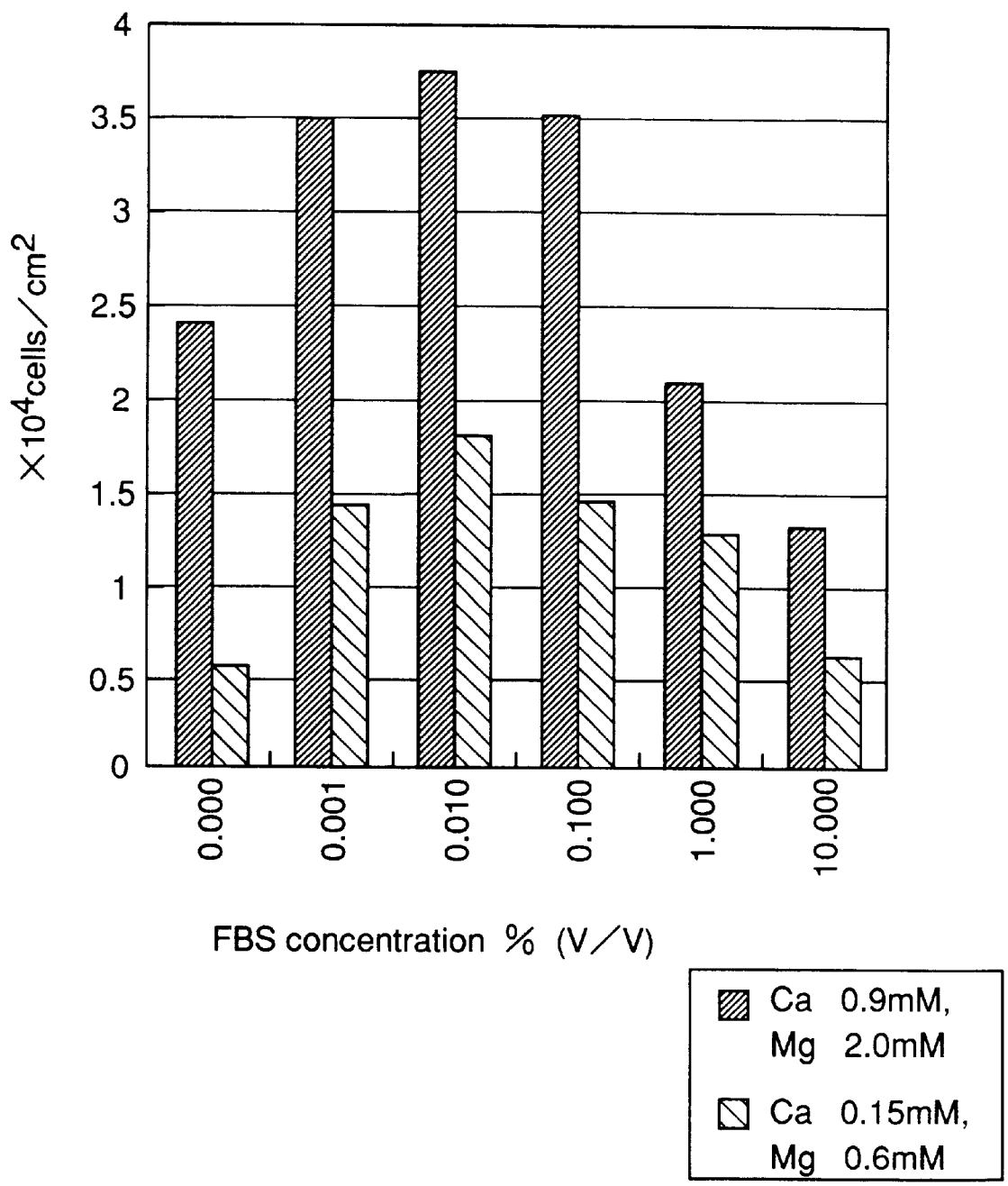
FIG. 12 represents results of example 7.

Normal human epidermal melanocyte were cultured using the above media according to the procedure of example 1. After 7 days incubation, the cells were harvested and cell numbers were determined. The results are shown in FIG. 11.

TABLE 8

Components of basal medium of example 6

| Component | mg/l |
|---|---|
| L-Alanine | 9 |
| L-Arginine.HCl | 211 |
| L-Asparagine.H$_2$O | 15.01 |
| L-Aspartic Acid | 13 |
| L-Cystine | 25 |
| L-Glutamic Acid | 14.7 |
| L-Glutamine | 146 |
| Glycine | 7.51 |
| L-Histidine HCl.H$_2$O | 23 |
| L-Isoleucine | 2.6 |
| L-Leucine | 13 |
| L-Lysine.HCl | 29 |
| L-Methionine | 4.48 |
| L-Phenylalanie | 5 |
| L-Proline | 11.5 |
| L-Serine | 10.5 |
| L-Threonine | 3.57 |
| L-Tryptophan | 0.6 |
| L-Tyrosine | 1.81 |
| L-Valine | 3.5 |
| d-Biotin | 0.024 |
| Folic Acid | 1.32 |
| DL-α-Lipoic Acid | 0.2 |
| Nicotinamide | 0.615 |
| D-Pantothenate(Ca) | 0.715 |
| Pyridoxine.HCl | 0.206 |
| Riboflavin | 0.0238 |
| Thiamin HCl | 1 |
| Vitamin B$_{12}$ | 1.36 |
| Choline Chloride | 0.698 |
| D-Glucose | 1100 |
| myo-lnositol | 0.541 |
| Hypoxanthine | 4 |
| Sodium Pyruvate | 110 |
| Thymidine | 0.7 |
| CaCl$_2$.2H$_2$O | 44.1 |
| KCl | 285 |
| MgSO$_4$.7H$_2$O | 152.8 |
| NaCl | 7400 |
| Na$_2$HPO$_4$ | 153.7 |
| KH$_2$PO$_4$ | 83 |
| CuSO$_4$.5H$_2$O | 0.0025 |
| FeSO$_4$.7H$_2$O | 0.834 |
| ZnSO$_4$.7H$_2$O | 0.0288 |
| NaHCO$_3$ | 1200 |

TABLE 9

Final concentrations of Ca$^{2+}$ and Mg$^{2+}$

| medium No. | 1 | 2 | 3 | 4 | 5 |
|---|---|---|---|---|---|
| Ca$^{2+}$ (mM) | 0.3 | 0.95 | 0.95 | 1.15 | 1.15 |
| Mg$_{2+}$ (mM) | 0.65 | 0.65 | 5.5 | 0.65 | 5.5 |

Example 7

The modified MCDB153 medium shown in above table 2 supplemented with the substances shown in above table 3 was used. The medium contains 0.15 mM of Ca$^{2+}$ and 0.60 mM of Mg$^{2+}$. In addition, the medium containing 0.9 mM of Ca$^{2+}$ and 2.0 mM of Mg$^{2+}$ was prepared. Various amounts of FBS were added into the both of media to yield a final concentration of from 0.001 to 10% (v/v). Normal human epidermal melanocyte were cultured in the above respective media according to the procedure of example 1. After 6 days incubation, the cells were harvested and cell number were determined. The results were shown in FIG. 11.

A maximum proliferation of the cell was obtained With a medium containing 0.01% of FBS. At any concentration of FBS, the cell proliferation obtained with the $Ca^{2+}$ or $Mg^{2+}$ enriched media was superior to that of conventional media.

What is claimed is:

1. A medium for culturing normal human epidermal melanocytes in vitro, comprising a basal medium for culturing animal cells, $Ca^{2+}$ at a final concentration of between about 0.9 mM and about 1.2 mM, $Mg^{2+}$ at a final concentration of between about 1.2 mM and about 6.0 mM, and serum at a final concentration of between about 0.001% and about 0.1% (v/v).

2. The medium of claim 1, further comprising one or more growth factors useful for growth of normal human epidermal melanocytes.

3. The medium of claim 2, wherein the basal medium for animal cell culture is MCDB 153.

4. The medium of claim 1, further comprising bovine pituitary extract.

5. The medium of claim 4, wherein the basal medium for animal cell culture is MCDB 153.

6. The medium of claim 1, wherein the basal medium for animal cell culture is MCDB 153.

7. A medium for culturing normal human epidermal melanocyte in vitro, comprising a basal medium for culturing animal cells, $Ca^{2+}$ at a final concentration of between about 0.15 mM and about 1.2 mM, $Mg^{2+}$ at a final concentration of between about 1.2 mM and about 6.0 mM and serum at a concentration of between about 0.001% and about 0.1% (v/v).

8. The medium of claim 7, wherein the final concentration of $Ca^{2+}$ is between about 0.9 mM and about 1.2 mM and the final concentration of $Mg^{2+}$ is between about 1.2 mM and 6.0 mM.

9. The medium of claim 7, further comprising one or more growth factors useful for growth of normal human epidermal melanocytes.

10. The medium of claim 7, further comprising bovine pituitary extract.

11. The medium of claim 7, wherein the basal medium for animal cell culture is MCDB 153.

* * * * *

UNITED STATES PATENT AND TRADEMARK OFFICE
CERTIFICATE OF CORRECTION

PATENT NO. : 5,916,809
DATED : June 29, 1999
INVENTOR(S) : Hiroshi YANASE et al.

It is certified that error appears in the above-identified patent and that said Letters Patent is hereby corrected as shown below:

On the title page

Assignee [73] wherein "Nec Corporation, Tokyo Japan" should be deleted and Assignee [73] should read --KURASHIKI BOSEKI KABUSHIKI KAISHA, Kurashiki-shi, Japan--.

Signed and Sealed this

Twenty-second Day of August, 2000

Attest:

Q. TODD DICKINSON

*Attesting Officer*  *Director of Patents and Trademarks*